United States Patent
Davis et al.

(10) Patent No.: US 7,572,625 B2
(45) Date of Patent: Aug. 11, 2009

(54) MEDICAL DEVICES COATED WITH DRUG CARRIER MACROMOLECULES

(75) Inventors: Liza J. Davis, St. Michael, MN (US); Kim Robertson, Forest Lake, MN (US); Richard C. Tooley, Jr., Crystal, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/435,690

(22) Filed: May 18, 2006

(65) Prior Publication Data

US 2007/0269479 A1    Nov. 22, 2007

(51) Int. Cl.
*C12M 3/00* (2006.01)
(52) U.S. Cl. .................................... 435/287.2
(58) Field of Classification Search ............. 435/287.2, 435/422–426; 424/422–424, 425, 426; 604/507
See application file for complete search history.

(56) References Cited

U.S. PATENT DOCUMENTS

| 4,886,062 | A | 12/1989 | Wiktor et al. | |
|---|---|---|---|---|
| 5,059,166 | A | 10/1991 | Fischell et al. | |
| 5,851,230 | A | 12/1998 | Weadock et al. | |
| 2003/0082105 | A1 * | 5/2003 | Fischman et al. | 424/9.6 |
| 2003/0229393 | A1 | 12/2003 | Kutryk et al. | |
| 2004/0029268 | A1 | 2/2004 | Colb et al. | |
| 2005/0043787 | A1 | 2/2005 | Kutryk et al. | |
| 2006/0078493 | A1 | 4/2006 | von Oepen | |

FOREIGN PATENT DOCUMENTS

| WO | WO-2002-067849 A | 9/2002 |
|---|---|---|
| WO | WO-2003-065881 A | 8/2003 |
| WO | WO-2005-027990 A | 3/2005 |
| WO | WO-2005-086831 A | 9/2005 |
| WO | WO-2005-097186 A | 10/2005 |

OTHER PUBLICATIONS

International Search Report for PCT/US2007/010646 dated Oct. 23, 2008.

* cited by examiner

*Primary Examiner*—Ann Y. Lam
(74) *Attorney, Agent, or Firm*—Kenyon & Kenyon LLP

(57) ABSTRACT

A medical device coated with carrier macromolecules, wherein the carrier macromolecules are conjugated with a therapeutic agent. The carrier macromolecules may be antibodies which bind the therapeutic agent at the antigen binding site or by covalent bonding. The carrier macromolecules may be tethered to the surface of or dispersed within a coating on the medical device. The carrier macromolecules may release the therapeutic agent upon exposure to a trigger, which may be exposure to an aqueous environment, or a change in the pH or the ionic strength of the environment. The carrier macromolecules may also be bispecific antibodies directed to both a therapeutic agent and a target antigen. In some cases, binding of the target antigen causes the therapeutic agent to be released from the bispecific antibody. Also provided are methods of controlling the release and targeting of therapeutic agents eluted from a medical device.

20 Claims, 2 Drawing Sheets

MEDICAL DEVICES COATED WITH DRUG CARRIER MACROMOLECULES

TECHNICAL FIELD

The present invention relates to drug-coated medical devices.

BACKGROUND

Many implantable medical devices are coated with drugs that are eluted from the medical device upon implantation. For example, some vascular stents are coated with a drug which is eluted from the stent for treatment of the vessel and/or to prevent some of the unwanted effects and complications of implanting the stent. In such drug-eluting medical devices, various methods have been proposed to control the release and targeting of the eluted drug. However, because such methods have certain disadvantages, there is a need for an improved method of controlling the release and targeting of drugs eluted from medical devices.

SUMMARY OF THE INVENTION

The present invention provides a medical device coated with carrier macromolecules, wherein the carrier macromolecules are conjugated with a therapeutic agent. In an embodiment, the carrier macromolecules are antibodies or antibody fragments. In some embodiments, the therapeutic agent is conjugated to the antibodies at the antigen binding site, whereas in other embodiments, the therapeutic agent is conjugated to the antibodies via a covalent bond. In certain embodiments, the antibodies release the therapeutic agent upon exposure to a trigger. In certain embodiments, the antibodies are bispecific antibodies.

The carrier macromolecules may be dispersed within a coating on the medical device and the carrier macromolecules may diffuse out of the coating or be affixed to the coating. Also provided are methods of controlling the release and targeting of therapeutic agents eluted from a medical device.

DETAILED DESCRIPTION

Figure 1:
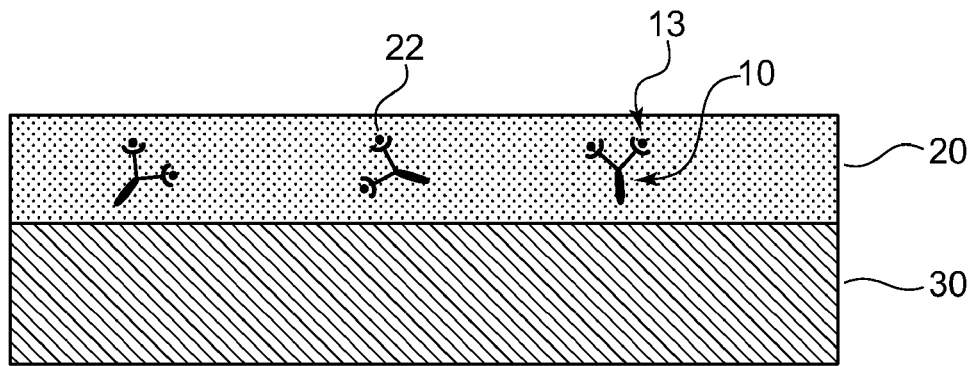
FIG. 1 is a cross-section schematic representation of a fragmentary portion of a medical device according to an embodiment of the present invention.

The present invention provides a medical device having a coating of carrier macromolecules disposed thereon wherein the carrier macromolecules carry therapeutic agents. In an embodiment of the present invention, the carrier macromolecules are antibodies. As used herein, the term antibody refers to an immunoglobulin, whether produced naturally or synthetically (e.g. recombinant), either in whole or in part. The term antibody also encompasses antibody fragments, which refers to any derivative of an antibody that is less than full length while retaining at least a portion of the full-length antibody's specific binding ability. Examples of antibody fragments include, but are not limited to, Fab, Fab', F(ab)$_2$, F(ab')$_2$, Fv, dsFv, single-chain Fvs (scFv), diabodies, and bispecific antibodies. The fragment can include multiple chains linked together. As used herein, an Fv antibody fragment is composed of one variable heavy domain ($V_H$) and one variable light ($V_L$) domain linked by noncovalent interactions. As used herein, a dsFv refers to an Fv with an engineered intermolecular disulfide bond which stabilizes the $V_H$-$V_L$ pair. As used herein, scFv refer to antibody fragments that contain a variable light chain ($V_L$) and variable heavy chain ($V_H$) covalently bonded by a polypeptide linker in any order. The linker is of a length such that the two variable domains are bridged without substantial interference. Exemplary linkers are (Gly-Ser)$_n$ residues with some Glu or Lys residues dispersed throughout to increase solubility. As used herein, diabodies are dimeric scFv.

Hence, antibody includes any protein having a binding domain that is homologous or substantially homologous to an immunoglobulin binding domain. The antibodies can be monoclonal antibodies (including full length monoclonal antibodies), polyclonal antibodies, or multispecific antibodies (e.g., bispecific antibodies). Antibodies include members of any immunoglobulin class, including IgG, IgM, IgA, IgD, and IgE.

In certain embodiments of the present invention, the antigen binding site of the antibodies is directed at therapeutic agents. In such embodiments, the antibodies carry the therapeutic agent by binding the therapeutic agent at the antigen binding site. Antibodies directed to therapeutic agents are commercially available or can be created by various methods known in the art. For example, the use of commercially available anti-paclitaxel antibodies of high affinity and high specificity is described in U.S. Pat. No. 5,981,777 (Durzan et al.), which is incorporated by reference herein.

In other embodiments, the therapeutic agent may be conjugated to the antibodies by covalent bonding. For example, a paclitaxel-antibody conjugate can be formed by reacting paclitaxel with glutaric anhydride to form 2'-glutaryl-paclitaxel having a cleavable ester bond. The 2'-glutaryl-paclitaxel is then activated by removal of a hydroxyl group in a carbodiimide reaction. The antibody then forms an amide bond to the activated 2'-glutaryl-paclitaxel via an amino group. See Guillemard et al., Cancer Research 61:694-699 (2001), which is incorporated be reference herein.

In these embodiments, the antigen binding site of the antibodies may be directed to various targets, which include, but are not limited to, components of connective tissue or extracellular matrix such as glycoproteins, collagen, or fibrin; or components on or within cell membranes, such as surface antigens, receptors, proteins, lipids, carbohydrates, and molecules processed on the cell surface. For example, the antibodies may be targeted to cell surface components of white blood cells, endothelial cells, or smooth muscle cells of the arterial wall.

In certain embodiments of the present invention, the therapeutic agent can be released from the carrier macromolecule. This release may be triggered by various events or conditions, such as exposure to an aqueous environment, or a change in the pH or ionic strength of the environment. For example, the carrier macromolecule may be an antibody directed to a therapeutic agent, where the antibody's binding affinity for the therapeutic agent decreases with a change in the pH or ionic strength of the environment. The release of therapeutic agent may also be triggered by temperature, magnetic fields, ultrasound, or osmotic pressure.

In other embodiments, the therapeutic agent is not released from the carrier macromolecules. In such instances, the carrier macromolecule-therapeutic agent complex itself may be the biologically active agent. For example, paclitaxel-antibody conjugates have been shown to be a potent cytotoxic agent. See Guillemard et al., Cancer Research 61:694-699 (2001), which is incorporated be reference herein.

In certain embodiments, the carrier macromolecules are bispecific antibodies. As used herein, bispecific antibodies are antibodies constructed to have two antigen binding sites, each directed to a different antigen or a different part of an antigen. Methods for making bispecific antibodies are known in the art. For example, bispecific antibodies can be made by fusing hybridoma lines expressing two different antibodies or by recombinant methods that join two antibody fragments containing different antigen binding sites.

A bispecific antibody used in the present invention has a first antigen binding site that is directed to a therapeutic agent, such as paclitaxel, and a second antigen binding site that is directed to a target antigen. The target antigen may be any type of antigen such as an organic compound, inorganic compound, metal complex, receptor, enzyme, antibody, protein, nucleic acid, peptide nucleic acid, DNA, RNA, polynucleotide, oligonucleotide, oligosaccharide, lipid, lipoprotein, amino acid, peptide, polypeptide, peptidomimetic, carbohydrate, enzyme cofactor, drug, prodrug, lectin, sugar, glycoprotein, biomolecule, macromolecule, biopolymer, polymer, and other such biochemical or biomolecular components. For example, the target antigen may be cell surface components of white blood cells, platelets, endothelial cells, or smooth muscle cells of the arterial wall; or biomolecules released in response to an unstable arterial plaque, such as thrombin or clotting factors.

In some embodiments, binding of the target antigen to the second binding site will decrease the first binding site's affinity for the therapeutic agent such that the therapeutic agent is released from the antibody. This loss of affinity for the therapeutic agent may occur through a conformational change in the antibody structure caused by the binding of the target antigen. One of skill in the art could screen bispecific antibodies and select for those having the desired properties.

The carrier macromolecules may be applied onto a medical device by various means. In the embodiment shown in FIG. 1, the carrier macromolecules are antibodies 10 which are dispersed within a coating 20 on a portion 30 of a medical device. Therapeutic agents 22 are conjugated to antibodies 10 at antigen binding site 13. In this exemplary embodiment, antibodies 10 are embedded in coating 20 in such a manner that antibodies 10 do not diffuse out of coating 20. As previously described herein, antibodies 10 can be triggered to release therapeutic agent 22. Thereupon, therapeutic agent 22 can diffuse out of coating 20 and be eluted into the surrounding fluid or tissue.

Coating 20 may be any coating used in coating medical devices, such as the polymer coatings used in drug-eluting vascular stents that are known in the art. Antibodies 10 may be incorporated into coating 20 by various methods, including those similar to the process of drug coating vascular stents. For example, antibodies 10 may be mixed into a solvent containing a polymer and the resultant mixture may be applied onto the medical device by spraying, dipping, roll coating, or the like.

Figure 2:
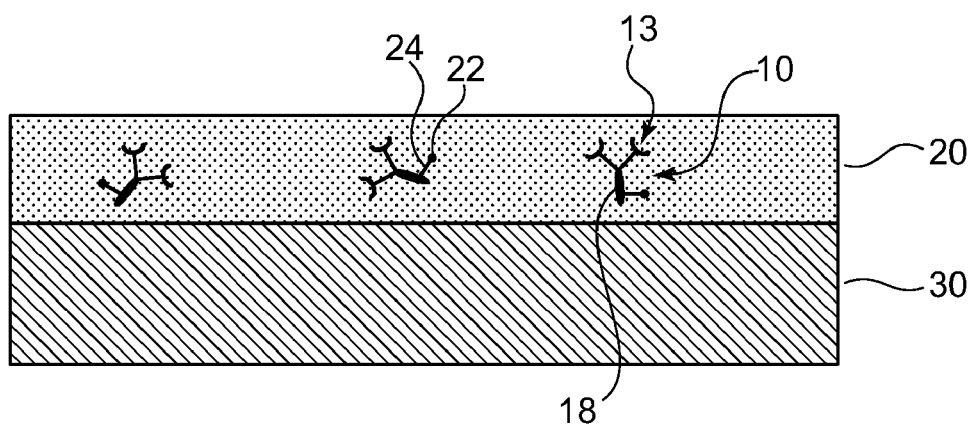
FIG. 2 is a cross-section schematic representation of a fragmentary portion of a medical device according to another embodiment.

In another embodiment shown in FIG. 2, the carrier macromolecules are antibodies 10 which are dispersed within a coating 20 on a portion 30 of a medical device. Therapeutic agents 22 are conjugated to antibodies 10 via covalent links 24. In this exemplary embodiment, the antibody-therapeutic agent complex diffuses out of coating 20 and elutes into the surrounding fluid or tissue. As described previously herein, antigen binding site 13 may be directed to a variety of target antigens.

Figure 3:
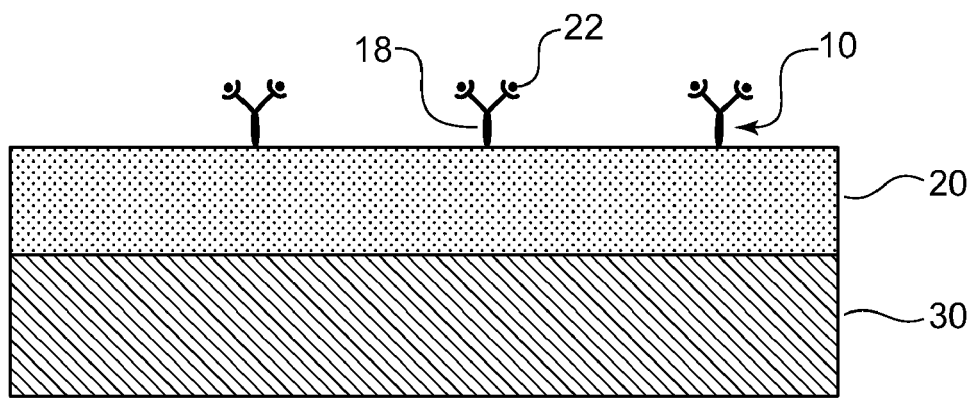
FIG. 3 is a cross-section schematic representation of a fragmentary portion of a medical device according to yet another embodiment.

In yet another embodiment shown in FIG. 3, the carrier macromolecules are antibodies 10 which are tethered to the surface of a coating 20 on a portion 30 of a medical device. In this exemplary embodiment, the Fc portion 18 of antibodies 10 are tethered to coating 20 by covalent linkages, such as those described in U.S. Patent Publication No. 2005/0043787 (Kutryk et al.), which is incorporated by reference herein.

Figure 4A:
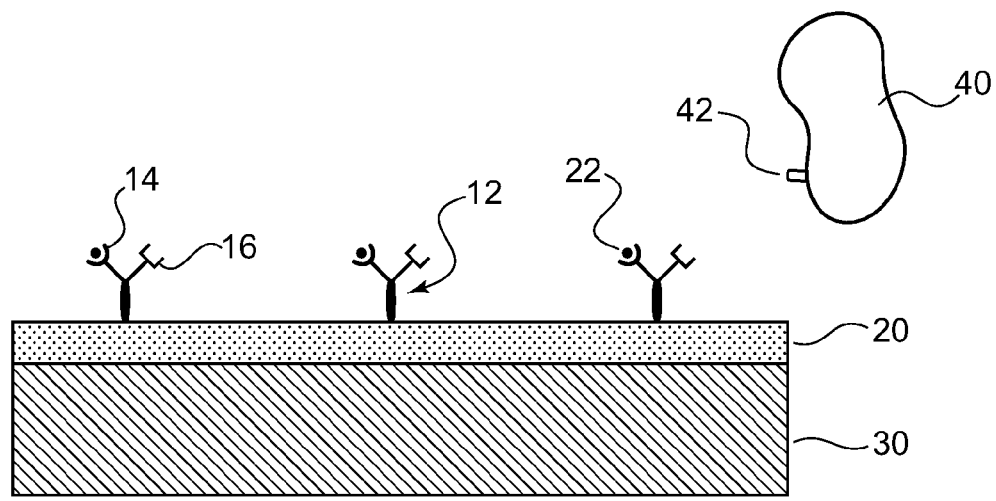
FIG. 4A is a cross-section schematic representation of a fragmentary portion of a medical device according to yet another embodiment where the carrier macromolecules are bispecific antibodies.
Figure 4B:
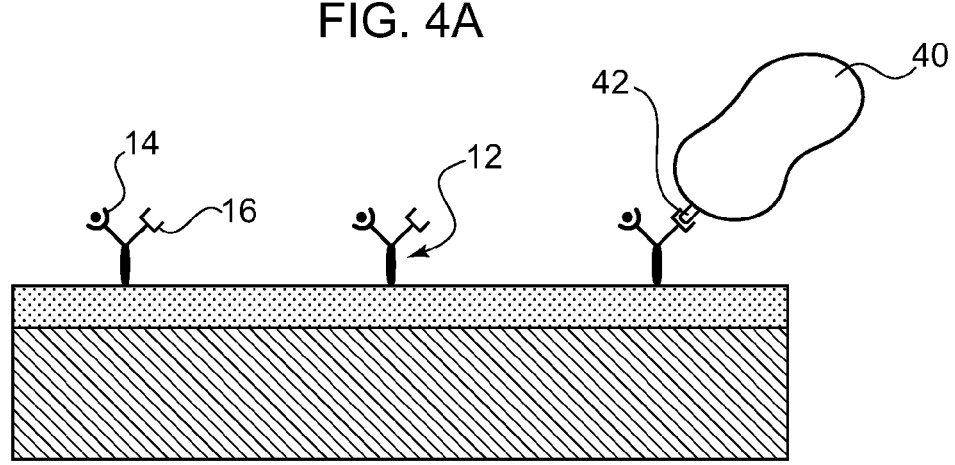
FIG. 4B is a cross-section schematic representation of the medical device of FIG. 4A showing a bispecific antibody binding to a cell surface antigen.
Figure 4C:
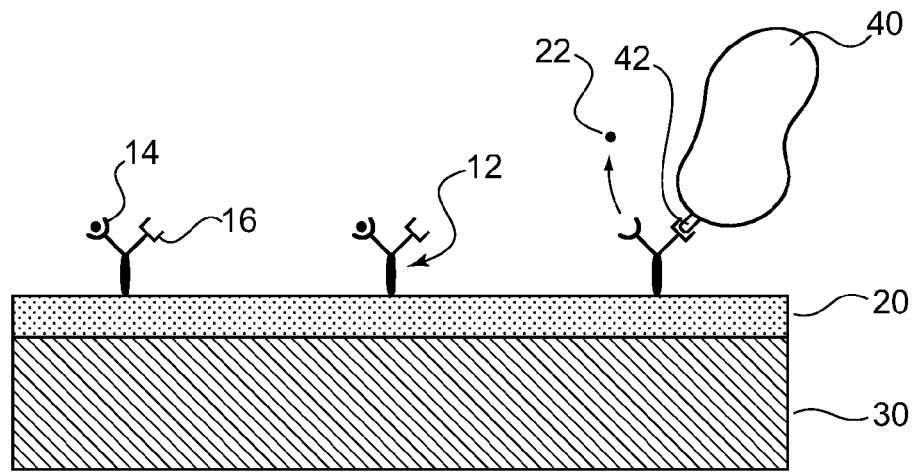
FIG. 4C is a cross-section schematic representation of the medical device of FIG. 4B showing a bispecific antibody releasing the therapeutic agent.

In yet another embodiment shown in FIG. 4A, the carrier macromolecules are bispecific antibodies 12, which are tethered to the surface of a coating 20 on a portion 30 of a medical device. The first antigen binding site 14 of bispecific antibody 12 binds to therapeutic agents 22. As shown in FIG. 4B, the second antigen binding site 16 of bispecific antibody 12 binds to a cell surface component 42 on a cell 40. In certain instances, as shown in FIG. 4C, the binding of cell surface component 42 will cause bispecific antibody 12 to release therapeutic agent 22 (as shown by the arrow).

In certain embodiments, the carrier macromolecules may be contained in a porous coating or porous surface on a medical device, such as the porous layers created by the deposition of metallic oxide particles or the carbonization of polymer coatings. The carrier macromolecules may diffuse out of the porous layer or may be permanently embedded in the porous layer.

Various combinations of the aforementioned embodiments are possible using a plurality of different types of carrier macromolecules, different therapeutic agents, or different target antigens. Also, various combinations of the aforementioned embodiments are possible using different locations on a medical device. For example, in a vascular stent, the outer diameter of the stent may be coated with an antibody directed to a target antigen on a vascular smooth muscle cell, while the inner diameter of the stent may be coated with an antibody directed to a target antigen on an endothelial cell. Furthermore, the antibody on the outer diameter may be conjugated to a different therapeutic agent than the antibody on the inner diameter. For example, the antibody on the outer diameter may be conjugated with an anti-proliferative drug, such as paclitaxel, while the antibody on the inner diameter may be conjugated to a growth factor, such as vascular endothelial growth factor (VEGF), or an anti-thrombotic drug such as heparin.

In another example, the end portions of a vascular stent may be coated with an antibody having high affinity for a therapeutic agent, while the central portions of the stent are coated with antibodies having lower affinity for the same therapeutic agent. In this embodiment, higher dosages of therapeutic agent would be released from the central portion of the stent compared to the ends of the stent where lower dosages are sufficient.

Any of the aforementioned embodiments may also be combined with free therapeutic agents which are not conjugated to a carrier macromolecule. For example, a polymer-coated vascular stent may have therapeutic agents that are not conjugated to carrier macromolecules dispersed within the coating and different therapeutic agents that are conjugated to carrier macromolecules either dispersed within the coating or affixed onto the surface of the coating.

Other examples of carrier macromolecules that can be used in the present invention include receptors, nuclear proteins, transcription regulators, enzymes, or cell-surface adhesion proteins.

The therapeutic agent conjugated to the carrier macromolecule may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as nonsteroidal anti-inflammatory agents and chelating agents such as ethylenediaminetetraacetic acid, O,O'-bis(2-aminoethyl) ethyleneglycol-N,N,N',N'-tetraacetic acid and mixtures thereof; antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMP's"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMP's are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin$^-$) cells including Lin$^-$CD34$^-$, Lin-CD34$^+$, Lin$^-$cKit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells. Any of the therapeutic agents may be combined to the extent such combination is biologically compatible.

The foregoing description and examples have been set forth merely to illustrate the invention and are not intended to be limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method of controlling the release of therapeutic agents from a medical device comprising the steps of:
   (a) providing a medical device having a coating of antibodies conjugated to a therapeutic agent, wherein the antibodies release the therapeutic agent upon exposure to a trigger;
   (b) implanting the medical device, with the coating of antibodies conjugated to the therapeutic agent, in a body; and
   (c) releasing the therapeutic agent by exposing the antibodies to the trigger.

2. The method of claim 1, wherein the antibodies are directed to the therapeutic agent and wherein the therapeutic agent is conjugated to the antibodies at the antigen binding site.

3. The method of claim 1, wherein the trigger is selected from the group consisting of exposure to an aqueous environment, a change in the pH of the environment, and a change in the ionic strength of the environment.

4. The method of claim 1, wherein the medical device is a stent.

5. The method of claim 1, wherein the antibodies are bispecific antibodies.

6. The method of claim 5, wherein the bispecific antibodies comprise a first antigen binding site directed to the therapeutic agent and a second antigen binding site directed to a target antigen.

7. The method of claim 6, wherein the therapeutic agent is conjugated to the bispecific antibody at the first antigen binding site, and wherein subsequent binding of the target antigen to the second antigen binding site causes a decrease in the first antigen binding site's affinity for the therapeutic agent such that the therapeutic agent is released from the bispecific antibody.

8. The method of claim 6, wherein the target antigen is a cell surface component of a white blood cell, platelet, endothelial cell, or vascular smooth muscle cell.

9. The method of claim 1, wherein the therapeutic agent is an anti-proliferative agent.

10. A method of targeting therapeutic agents released from a medical device comprising the steps of:
    (a) providing a medical device having a coating of carrier macromolecules conjugated to a therapeutic agent, wherein the carrier macromolecules have a binding site directed to a target antigen, wherein the target antigen is a component of body tissue;
    (b) implanting the medical device, with the coating of carrier macromolecules conjugated to the therapeutic agent, in a body; and
    (c) releasing at least the therapeutic agent from the medical device.

11. The method of claim 10, wherein the carrier macromolecule is an antibody.

12. The method of claim 11, wherein the therapeutic agent is covalently bound to the antibody.

13. The method of claim 12, wherein the target antigen is a cell surface component of a white blood cell, platelet, endothelial cell, or vascular smooth muscle cell.

14. The method of claim 11, wherein the antibodies are bispecific antibodies.

15. The method of claim 14, wherein the bispecific antibodies comprise a first antigen binding site directed to the therapeutic agent and a second antigen binding site directed to a target antigen.

16. The method of claim 10, wherein the medical device is a stent.

17. The method of claim 10, wherein the carriers macromolecules diffuse out of the coating.

18. The method of claim 10, wherein the carrier macromolecules are affixed to the surface of a coating on the medical device.

19. The method of claim 10, wherein the releasing comprises releasing the therapeutic agent and the carrier macromolecule.

20. The method of claim 10, wherein the therapeutic agent is an anti-proliferative agent.

* * * * *